US005994501A

United States Patent [19]
Ruoslahti et al.

[11] Patent Number: 5,994,501
[45] Date of Patent: *Nov. 30, 1999

[54] TETRAPEPTIDE

[75] Inventors: Erkki Ruoslahti, Olivenhain; Michael Pierschbacher, San Diego, both of Calif.

[73] Assignee: The La Jolla Cancer Research Foundation, La Jolla, Calif.

[*] Notice: This patent is subject to a terminal disclaimer.

[21] Appl. No.: 09/058,540

[22] Filed: Apr. 10, 1998

Related U.S. Application Data

[63] Continuation of application No. 08/458,833, Jun. 2, 1995, which is a continuation of application No. 07/902,472, Jun. 19, 1992, which is a continuation of application No. 07/660,526, Feb. 25, 1991, abandoned, which is a continuation of application No. 07/242,713, Sep. 9, 1988, Pat. No. 5,041,380, which is a continuation of application No. 06/744,981, Jun. 17, 1985, Pat. No. 4,792,525, which is a division of application No. 06/554,821, Nov. 22, 1983, Pat. No. 4,578,079, which is a continuation-in-part of application No. 06/405,239, Aug. 4, 1982, Pat. No. 4,517,686, which is a continuation-in-part of application No. 06/433,457, Oct. 8, 1982, abandoned, which is a continuation-in-part of application No. 06/518,036, Jul. 28, 1983, Pat. No. 4,589,881.

[51] Int. Cl.$^6$ .............................. C12N 11/08; C07K 5/00; C07K 17/02

[52] U.S. Cl. ..................... 530/324; 435/180; 530/330; 530/324; 530/812; 530/815; 530/811; 514/12; 514/13; 514/14; 514/15; 514/16; 514/17; 514/18

[58] Field of Search ................ 514/12–18; 530/330, 530/324, 811, 812, 815, 350, 382

[56] References Cited

U.S. PATENT DOCUMENTS

| | | | |
|---|---|---|---|
| 3,883,393 | 5/1975 | Knazek et al. | 435/240 |
| 4,511,653 | 4/1985 | Play et al. | 435/69 |
| 4,517,686 | 5/1985 | Ruoslahti | 3/1 |
| 4,578,079 | 3/1986 | Ruoslahti | 623/11 |
| 4,589,881 | 5/1986 | Pierschbacher et al. | 623/11 |
| 4,792,525 | 12/1988 | Ruoslahti | 435/180 |
| 5,041,380 | 8/1991 | Ruoslahti et al. | 435/240.2 |
| 5,278,063 | 1/1994 | Hubbell et al. | 435/240.243 |

OTHER PUBLICATIONS

Hynes, et al. Cell surface fibronectin and oncogenic transformation. *J. Supramolecular Structure* 11:95–104(1979).
Hahn, Lian–Hsien E. and Kenneth M. Yamada. Isolation and biological characterization of active fragments of the adhesive glycoprotein fibronectin. *Cell* 18:1043–1051, 1979.
Sekiguchi, Kiyotoshi and Sen–Itiroh Hakomori. Functional domain structure of fibronectin. *Proc. Natl. Acad. Sci.* 77:2661–2665.
Grinnell, Frederick, et al. Distribution of fibronectin during wound healing in Vivo. *J. Invest. Dermatol.* 76:181–189, 1981.
McDonagh, R.P., et al. Amino acid sequence of the factor XIII$_a$ acceptor site in bovine plasma fibronectin. *Febs Letters.* 127:174–178, 1981.

Ruoslahti, Erkki, et al. Alignment of biologically active domain in the fibronectin molecule. *J. Biol. Chem.* 256:7277–2781, 198–.
Pande, Hema, et al. Comparative structural studies of human plasma and amniotic fluid fibronectins. *Bioch, Biophy, Res. Comm.*101:265–272, 1981.
Pande, Hema and John E. Shively. NH$_2$–terminal sequences of DNA–heparin–, and gelatin–binding tryptic fragments from human plasma fibronectin. *Arch Bioch. Biophy.* 213:258–265, 1982.
Pierschbacher, Michael D., et al. The cell attachment domain fibronectin. *J. Biol. Chem.* 257:9593–9597, 1982.
Seitz, T.L. and K.D. Noonan. Effect of fibronectin on the adhesion of an established cell line to a surface reactive bio material. *J. Biomed. Mat. Res.* 16:195–207, 1982.
Vibe–Pedersen, Karen, et al. Amino acid sequence of a peptide from bovine plasma fibronectin containing a free sulfhydryl (cysteine). *Febs. Letters* 142:26–30, 1982.
Sekiguchi, Kiyotoshi, et al. Monoclonal antibodies directed to two different domains of human plasma fibronectin: Their specificities. *Fed. Eur. Bich. Soc.* 142:243–246, 1982.
Ehrismann, Ruth, et al. Arrangement of attachment–promoting, self–association, and heparin–binding sites in horse serum fibronectin. *J. Biol. Chem.* 257:7381–7387, 1982.
Clark, Richard A.F., et al. Fibronectin is produced by blood vessels in response to injury. *J. Exp. Med.* 156:646–651 1982.
Hynes, Richard O. and Kenneth M. Yamada. Fibronectins: Multifunctional modular glycoproteins. *J. Cell. Biol.* 95:369–377, 1982.
Petersen, Torbene, et al. Partial primary structure of bovine plasma fibronectin: Three types of internal homology. *Proc. Natl. Acad. Sci.* 80:137–141, 1983.
Grinnell, Frederick. Cell attachment and spreading factors in *Growth and Maturation Factors* (Dr. Gordon Guroff, Ed.) John Wiley & Sons, Inc., 1983.
Grinnell, Frederick. The role of fibronectin in the bioreaction of material surfaces in Biocompatible Polymers, Metals, and Composites. (Ed. Michael Szycher). Technomic Publishing, Lancaster, Pennsylvania 1983.
Hayashi, Masao and Kenneth M. Yamada. Domain structure of the carboxyl–terminal half of human plasma fibronectin. *J. Biol. Ch* 258:3332–3340, 1983.
Kornblihtt, Alberto R., et al. Isolation and characterization of cDNA clones for human and bovine fibronectins. *Proc. Natl. Acad. Sci.* 80:3218–3222, 1983.
Pierschbacher, Michael, et al. Synthetic peptide with cell attachment activity of fibronectin. *Proc. Natl. Acad. Sci.* 80:1224–12 1983.
Grinnell et al., *Cell,* 19:517–525 (1980).
Bernard et al., *Biochemistry,* 22:5213–5223 (1983).
Seyer et al., *Biochem.,* 20:2621–2727 (1981).

*Primary Examiner*—F. T. Moezie
*Attorney, Agent, or Firm*—Campbell & Flores LLP

[57] ABSTRACT

The peptide X-Arg-Gly-Asp-R-Y wherein X is H or at least one amino acid and Y is OH or at least one amino acid, and R is an amino acid selected from Thr or Cys, or other amino acid, having the same cell-attachment activity as fibronectin and the peptide X-Arg-Gly-Asp-Ser-Y, wherein X and Y, having said activity are disclosed.

11 Claims, 3 Drawing Sheets

| CODE | SEQUENCE | CELL ATTACHMENT 0.10 nmol/ml (++++) |
|---|---|---|
| FIBRONECTIN | | 0.25 |
| IV | YAVTGRGDSPASSKPISINYRTEIDKPSQM(C) | |
| IVA | VTGRGDSPASSKPI(C) | 1.6 |
| IVB | SINYRTEIDKPSQM(C) | >50.0 |
| IVA1 | VTGRGDSPA(C) | 2.5 |
| IVA2 | SPASSKPIS(C) | >50.0 |
| IVA1a | VTGRGD(C) | 10.0 |
| IVA1b | GRGDS(C) | 3.0 |
| IVA1c | RGDSPA(C) | 6.0 |
| RVDS | RVDSPA(C) | >50.0 |
| TGRG | TGRG | – |
| RGDS | RGDS | ++ |
| GDSP | GDSP | – |

| A) PROTEINS | SEQUENCE | CELL ATTACHMENT |
|---|---|---|
| Fibronectin | A V T G R G D S P A S S K | Active |
| Fibronectin α chain | T S Y N R G D S T F E S K | Active |
| λ receptor on E. coli | G S F G R G D S D E W T F | NT§ |
| Sindbis coat protein | G V G G R G D S A R P I M | NT |
| α lytic protease | A C M G R G D S A G S W I | NT |
| Testis-specific basic protein | K S R K R G D S A D R N Y | NT |
| B) Collagens: | | |
| α2(I)T | A P G L R G D T G A T G R | Active |
| α2(I)K | P Q G I R G D K G E P G E | Inactive |
| α1(IV)P | D X G S R G D P*G T P*G V | Inactive |
| α1(II)KE | A P*G V K G E S G S P G S | Inactive |

§ Not Tested
\* 4-hydroxyproline

TETRAPEPTIDE

This application is a continuation of application Ser. No. 08/458,833 now pending, filed Jun. 2, 1995, which is a continuation of application Ser. No. 07/902,472, filed Jun. 19, 1992 now pending, which is a continuation of application Ser. No. 07/660,526, filed Feb. 25, 1991 now abandoned, which is a continuation of application Ser. No. 07/242,713, filed Sept. 9, 1988, issued as U.S. Pat. No. 5,041,380; which is a continuation of application Ser. No. 06/744,981, filed Jun. 17, 1985, issued as U.S. Patent No. 4,792,525, which is a divisional of application Ser. No. 06/554,821, filed Nov. 22, 1983, issued as U.S. Pat. No. 4,578,079; which is a continuation-in-part of application Ser. No. 06/405,239, filed Aug. 4, 1982, issued as U.S. Pat. No. 4,517,686; which is a continuation-in-part of application Ser. No. 06/433,457 filed Nov. 8, 1982, now abandoned; which is continuation-in-part of application Ser. No. 06/518,036, filed Jul. 28, 1983, issued as U.S. Pat. No. 4,589,881.

This invention is directed to polypeptides related to fibronectin and more particularly to a polypeptide segment of human fibronectin which interacts with cell surfaces. In particular, the invention promotes cell attachment to substrates on which the peptide segment is immobilized, and inhibits cell attachment when presented in solubilized form.

BACKGROUND OF THE INVENTION

Fibronectin is a large glycoprotein, about 450 thousand daltons, which is composed of several apparently independent functional domains. Fibronectin was earlier discovered as a major extracellular matrix protein, and it was demonstrated that it would interact in vitro with other structural molecules, such as collagen, glycosaminoglycans, proteoglycans, fibrinogen, fibrin, and actin, as well as with cell surfaces. It was discovered that fibronectin promotes the attachment of suspended cells to collagen and also that it promotes the attachment of suspended cells directly to tissue culture substrate, independent of its binding to collagen. Accordingly, investigation continued with respect to the region of the fibronectin molecule that interacts with cell surfaces.

Earlier, a polypeptide fragment of fibronectin which embodies the cell attachment activity of fibronectin was isolated, purified and characterized as a 11.5 kDal polypeptide of 108 amino acid residues, and having the formula: H-Ile-Gly-Gln-Gln-Set-Thr-Val-Ser-Asp-Val-Pro-Arg-Asp-Leu-Glu-Val-Val-Ala-Ala-Thr-Pro-Thr-Ser-Leu-Leu-Ile-Ser-Trp-Asp-Ala-Pro-Ala-Val-Thr-Val-Arg-Tyr-Tyt-Arg-Ile-Thr-Tyr-Gly-Glu-Thr-Gly-Gly-Asn-Ser-Pro-Val-Gln-Glu-Phe-Thr-Val-Pro-Gly-Ser-Lys-Ser-Thr-Ala-Thr-Ile-Ser-Gly-Leu-Lys-Pro-Gly-Val-Asp-Tyr-Thr-Ile-Thr-Val-Tyr-Ala-Val-Thr-Gly-Arg-Gly-Asp-Ser-Pro-Ala-Ser-Ser-Lys- Pro-Ile-Ser-Ile-Asn-Tyr-Arg-Thr-Glu-Ile-Asp-Lys-Pro-Ser-Gln-Met-OH. Also, a fragment of the foregoing molecule having the same cell attachment activity was synthesized and is comprised of 30 amino acid residues having the formula: H-Tyr-Ala-Val-Thr-Gly-Arg-Gly-Asp-Ser-Pro-Ala-Ser-Ser-Lys-Pro-Ile-Ser-Ile-Asn-Tyr-Arg-Thr-Glu-Ile-Asp-Lys-Pro-Ser-Gln-Met-OH. (These fragments have been described in the aforesaid patent applications.) These polypeptides, or a fragment thereof which has cell attachment activity, can be used to prepare substrates to which cells will attach. Such substrates are useful in cell culture dishes and are also useful for employment in medical prosthetic devices for implantation in the human body where enhanced cell attachment to the surface is desirable.

SUMMARY OF THE INVENTION

Here we wish to describe the precise localization of this function of the fibronectin molecule as a tetrapeptide sequence. This sequence or a chemically similar, biologically equivalent, sequence is shared by some other proteins which interact with cells. These include collagen, fibrinogen and surface proteins of E. coli bacteria and Sindbis virus. These findings suggest that the mechanism by which cells attach to a fibronectin-containing substrate may be only one instance of a widely general recognition system that cells use to adhere to any number of substrates. This mechanism may also be involved with a cell's phagocytic activity. Further, it also appears possible that bacteria and possibly even certain viruses may take advantage of this universal cellular adhesion mechanism to gain entry into the body or the cell.

The present invention contemplates a new composition, a polypeptide which alters the cell attachment activity of cells to various substrates independent of its binding to collagen, affects cell phagocytosis, and which consists essentially of an isolated tetrapeptide X-Arg-Gly-Asp-Ser-Y wherein X is H or one or more amino acids and Y is OH or one or more amino acids. The tetrapeptide composition is characterized in that it is substantially isolated from fibronectin, either by separation from fibronectin or by synthesis wherein fibronectin was never present, and has substantially the same cell attachment activity as fibronectin. In defining the tetrapeptide, there is some variability in one of the amino acids. While Arg-Gly-Asp-Ser is the preferred form of the tetrapeptide of this invention, it may include other amino acids additionally or in a limited sense in substitution for one or more of the amino acids, such as for Ser, Arg-Gly-Asp-Cys or Arg-Gly-Asp-Thr which exhibit a similar cell attachment activity. Chemical moieties may be included at either end, typically at the —COOH end, of the, tetrapeptide for the purpose of immobilizing the peptide, or, amino acid additions may be used to modify the cell attachment activity. Also, the invention may be incorporated as part of a larger molecule.

The present invention also contemplates the method of using these compositions to promote cell attachment to a substrate wherein the invention is immobilized on the substrate.

The present invention additionally contemplates the method of using the invention in a solubilized or suspended form to inhibit undesirable cell attachment to a substrate or to each other, and to enhance the phagocytic activity of the cells.

DESCRIPTION OF THE DRAWINGS

FIG. 1 lists the polypeptides, and their respective amino acid sequence and relative cell attachment activity in concentrations necessary to achieve half-maximal activity, that were synthesized in determining the smallest peptide exhibiting cell attachment activity.

FIG. 3 lists the proteins ocurring naturally containing substantially the tetrapeptide sequence of amino acids, the fragment sequence synthesized (in bold type) containing the active site, and the cell attachment activity if tested.

Figure 2:
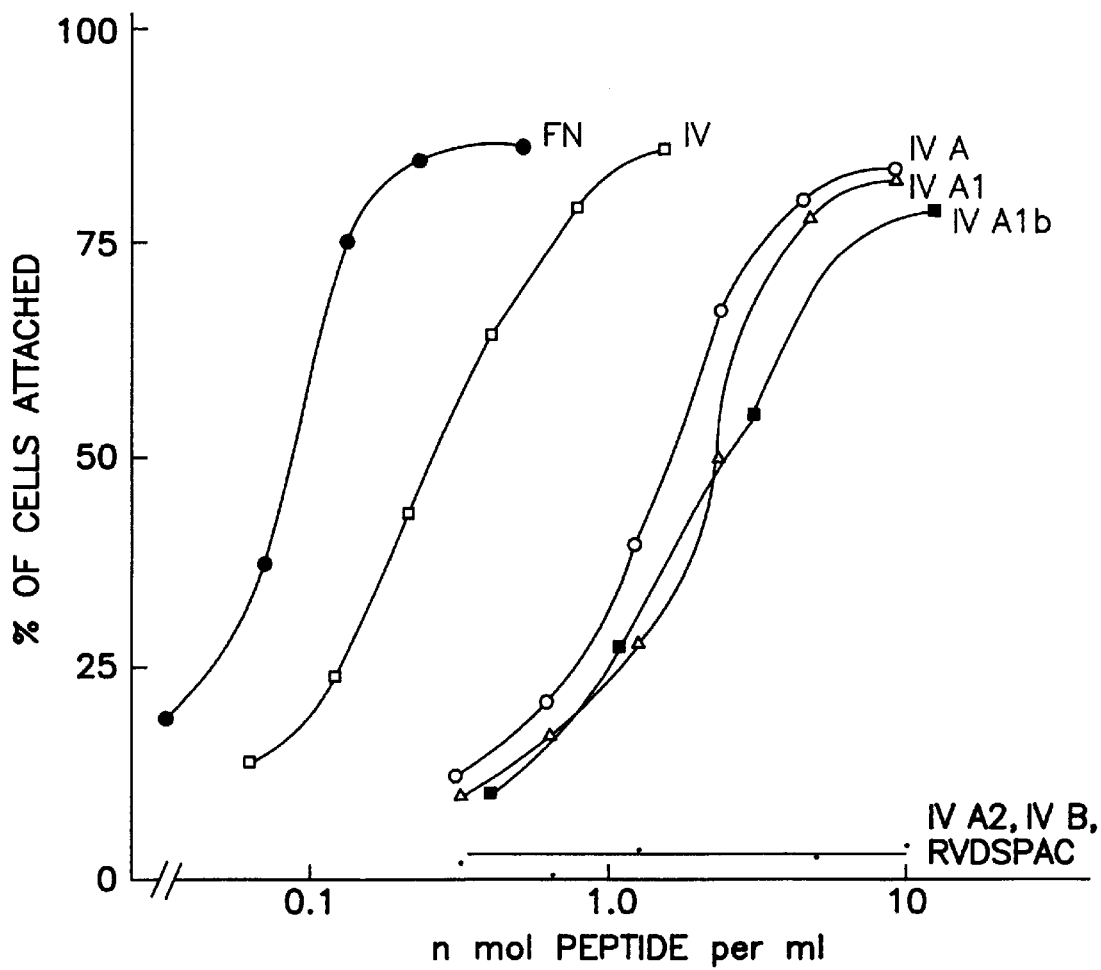
FIG. 2 compares cell attachment activity of selected synthesized polypeptides from FIG. 1 with fibronectin (FN).

| Abbreviations for Amino Acids | | |
|---|---|---|
| Amino Acid | Three-letter abbreviation | One-letter symbol |
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The nomenclature used to define the polypeptide is that specified by Schroder & Lubke, "The Peptides", Academic Press (1965) wherein, in accordance with conventional representation the N-terminus appears to the left, and the C-terminus appears to the right. Where the amino acid residue has isomeric forms, it is the L-form of the amino acid that is represented.

The Lnvention provides a polypeptide having the following formula: H-Arg-Gly-Asp-Ser-OH and is intended to include other polypeptides or substances containing this formula as well as polypeptides formed from the invention by limited substitution or deletion and which have cell attachment activity. (Cell attachment activity hereinafter includes cell attachment promoting activity, phagocytic activity, and the inhibition of cell attachment.) Moreover, the coupling of the peptide to substrates may be faciliated in certain instances, without affecting the cell attachment activity, by adding a Cys residue at the C-terminus. Further, the cell attachment activity may be modulated by variable additions to the C- and/or N-termini.

The invention, or a larger polypeptide or other molecule including the invention, can be synthesized by any suitable method, such as by exclusively solid-phase techniques, by partial solid-phase techniques, by fragment condensation, or by classical solution addition. It is also envisioned that a hybrid protein with adhesive or cell attachment properties could be generated by combining the peptide of the invention with another protein. Moreover, using recently developed recombinant DNA techniques, the invention may be synthesized singularly, or combined with another protein by first including the DNA code of the invention in the code of the desired protein.

Source of Peptides. The peptides are preferably prepared using solid phase synthesis, such as that described by Merrifield, *J. Am. Chem. Soc.,* 85, 2149 (1964), although other equivalent chemical syntheses known in the art, as mentioned above, can also be used. Solid-phase synthesis is commenced from the C-terminus of the peptide by coupling a protected alpha-amino acid to a suitable resin, as generally set forth in U.S. Pat. No. 4,244,946, issued Jan. 21, 1982 to Rivier et al., the disclosure of which is incorporated herein by reference. Examples of syntheses of this general type are set forth in U.S. Pat. Nos. 4,305,872 and 4,316,891. Discussion of the solid-prase synthesis of a 41-residue polypeptide is set forth in *Science,* 213, 1394–1397 (Sept. 1981) in an article by Vale et al., which refers to a more detailed discussion of the synthesis, which appears in an article by Marki et al. in *J. Am. Chem. Soc.,* 103, 3178 (1981).

In order to locate the cell attachment activity of the fibronectin molecule which would possibly be contained within a hydrophilic stretch of amino acids in the 30-amino acid synthetic peptide described above, a number of peptides were synthesized using the Merrifield procedure by Peninsula Laboratories (Belmont, Calif.), and included, in most cases, a COOH-terminal cystine. The design was to selectively synthesize peptides smaller than a previous fragment exhibiting cell attachment activity. As can be clearly seen in FIG. 1, this approach permits the determination of the smallest fragment showing activity.

Cell Attachment Promoting Activity. Those peptides having a COOH-terminal cystine residue were assayed for their activity in promoting cell attachment by first attaching them via the heterobifunctional crosslinker SPDP (N-succinimidyl 3-(2-pyridyldithio) propionate, Sigma, St. Louis, Mo.) to rabbit IgG which was immobilized on plastic. The attachment assay was then carried out as described by Ruoslahti, E. et al., Methods Enzymology 82: 803–831 (1981) using freshly trypsinized normal rat kidney cells (NRK). After a one hour incubation, those cells which had attached were fixed, stained and quantitated using either an Artek cell counter or a multiscan spectrophotometer. In all cases, maximum attachment was about 80–90% of the cells plated. The relative activity of each peptide is indicated by the concentration of the peptides in nmoles/ml necessary to achieve half-maximal activity, or, where accurate quantitation was not possible, by the crosses at the right of FIG. 1, and by the graph in FIG. 2.

Among the peptides tested, the tetrapeptide Arg-Gly-Asp-Ser was the smallest one and the only tetrapeptide which, when properly immobilized, had the property of causing cell attachment. The activity of the peptides decreased somewhat with size (FIG. 2). This decrease may be due to a decrease in the stability of their conformation or to a relative inaccessibility on the substrate. The serine residue could be replaced by a cysteine residue without complete loss of the activity of the peptide. When the arginine or aspartic acid residues were selectively deleted, however, the activity was lost. Moreover, substitution of the glycine with the bulky valine residue also abolished the activity (RVDSPAC, FIG. 1). Whereas these results show that the residues critical for the activity reside in the tetrapeptide sequence, amino acids immediately flanking the four residue fragment may have a modulatory effect on their activity.

It appears that while the tetrapeptide described is the determinant, optimum size of the polypeptide is about a hexapeptide which includes the defined tetrapeptide. Thus, the invention consists essentially of the tetrapeptide which would preferably be part of a hexapeptide.

Arg-Gly-Asp-Ser and Related Sequences in Other Proteins. Having established the importance of the tetrapeptide sequence, a computer search through the published protein sequences was conducted by the National Biomedical Research Foundation (George Washington University Medical Center, Washington, D.C.). Also included were sequences in which the serine was allowed to be replaced by other amino acids, and the arginine and aspartic acid by the chemically similar lysine and glutamic acid, respectively. The search through other proteins revealed five proteins having the Arg-Gly-Asp-Ser sequence (FIG. 3).

Of the five proteins having the identical four amino acid sequence, fibrin(ogen) is of most obvious interest because of its demonstrated interaction with fibronectin and cell surfaces. For this reason, a synthetic nonopeptide designed after the fibrin sequence was tested. As can be seen in FIG. 3, it too was an active cell attachment promoter. Attempts to demonstrate the attachment of test cells to intact fibrinogen or fibrin have giver, no clear-cut results, although platelets do bind to the fibrinogen molecule.

Among the remaining proteins that possess sequences related to the active tetrapeptide, the family of collagenous proteins is of particular interest for two reasons. First, collagens have been shown to mediate cell attachment independently of fibronectin, and, secondly, variations of the tetrapeptide sequence are particularly abundant in collagens. These sequences are repeated at fairly regular intervals along the $\alpha_1$ and $\alpha_2$ chains of type I collagen.

Four synthetic peptides were prepared based on diverse sequences in collagen. In three of these, the serine residue was replaced by threonine, hydroxyproline, or lysine, respectively. In the fourth one a lysine was substituted for arginine and glutamic acid for aspartic acid. Of these peptides only the serine to threonine substitution was active with the NRK test cells (FIG. 2). Other chemically similar substitutions such as serine to alanine may also yield active sites.

The results show that the primary cell-binding site of the fibronectin molecule resides in an extremely short amino acid sequence which is shared by at least one other adhesive protein, collagen. Because of the nature of the proteins having the tetrapeptide sequence among the proteins searched, the results suggest that the tetrapeptide with selected substitutions, may represent a universal attachment mechanism.

Inhibition of Cell Attachment. If the mechanism of cell attachment involves the recognition of the amino acid sequence of the tetrapeptide by a receptor on the cell, then it could be postulated that attachment could be inhibited by preventing this recognition by "blockings" the receptor. To demonstrate this inhibitory function of the invention, fibronectin was immobilized on a substrate to be tested for cell attachment activity. In separate experiments, various concentrations of the tetrapeptide (Arg-Gly-Asp-Ser) and a hexapeptide, Pro-Arg-Gly-Asp-Ser-Gly in a solubilized form were combined with the free cells, and attachment activity measured as above. Both peptides were shown to inhibit the normal attachment of cells to a fibronectin-coated substrate when placed in a solubilized form in combination with the free cells. The concentration necessary to exhibit half-maximal cell inhibition activity was 0.6–0.8 mmoles/ml and 0.3 mmoles/ml for the tetrapeptide and the hexapeptide, respectively.

Enhanced Phagocytic Activity. Fibronectin has been shown to promote phagocytosis, and this activity has been linked to the cell attachment activity. An application that can be envisioned for the invention based on these observations is to promote the entrance to cells of particles containing, for example, a therapeutic agent, by administering the particles with the invention in a solubilized form.

Practical application such as the preparation of surfaces for optimal cell culture, the derivatization of various prosthetic materials to promote bonding with surrounding tissues, a method to provide for the increased internalization of molecules such as toxins, drugs, hormones, or the like by the enhancement of phagocytosis, and the development of ways of manipulating cellular adhesion mechanisms in diseases such as cancer metastasis and platelet aggregation can also be envisioned. Since a peptide of four amino acids is unlikely to have more than one binding site, one question that can be addressed now is whether the interaction of all types of cells with fibronectin involves this same region of the molecule. Platelets, for example, may bind fibronectin on their surfaces by a different mechanism. This would be important in using this peptide to regulate cell attachment or in the design of prosthetic materials. It would also shed light on the role played by fibronectin in vivo.

In particular, the coating of the culture substrate with the cell-attachment polypeptide obviates the use of fibronectin in the medium, thus providing better defined conditions for the culture as well as better reproducibility. As one example of commercial use of cell-attachment surfaces, Cytodex particles, manufactured by Pharmacia, are coated with gelatin, making it possible to grow the same number of adherent cells in a much smaller volume of medium than would be possible in dishes. The activity of these beads is generally dependent upon the use of fibronectin in the growth medium, and the cell-attachment polypeptide is expected to provide an improved, chemically-defined coating for such purposes. Other surfaces or materials may be coated to enhance attachment, such as glass, agarose, synthetic resins, or long-chain polysaccharides.

Medical devices can be designed making use of such substrata to attract cells to the surface in vivo or even to promote the growing of a desired cell type on a particular surface prior to grafting. An example of such an approach is the induction of endothelial cell growth on a prosthetic blood vessel or vascular graft, which is generally woven or knitted from nitrocellulose or polyester fiber, particularly Dacron (polyethylene terephthalate) fiber. Most types of cells are attracted to fibronectin and to this polypeptide, but endothelial cells and fibroblastic cells in particular are attracted to fibronectin. The latter point indicates the potential usefulness of this defined polypeptide in coating a patch graft or the like for aiding wound closure and healing following an accident or surgery. In such cases, it may be advantageous to couple the peptide to a biological molecule, such as collagen, a glycosaminoglycan or a proteoglycan; for example, the five-residue fragment having a Cys-residue at the C-terminus coupled to monomeric collagen by using a crosslinker such as 3-(2-pyridyldithilo) propionic acid N-hydroxysuccinimide ester to effect cross-linking of the cysteine to a lysine residue in the collagen, or by using carbodiimide without the Cys on the four-residue fragment. It is also indicative of its value in coating surfaces of a prosthetic device which is intended to serve as a temporary or semipermanent entry into the body, e.g. into a blood vessel or into the peritoneal cavity, sometimes referred to as a percutaneous device. Fibronectin has been shown to be chemotactic to fibroblasts and macrophages. This activity correlates with the presence of the cell attachment domain. One potential manifestation of the cell attachment activity of the synthetic peptides described here, and fragments thereof of like characteristics, is chemotactic activity.

Application of the ability of the invention to inhibit cell attachment when presented in a solubilized form may find utility in situations where it is desirable to prevent cell adhesion to a substrate or adhesion between cells. Undesirable cell attachment to various medical sutures, or dressings, may be prevented by presenting the invention in solubilized form. When the invention is used either in conjunction or combination with another molecule, such as a therapeutic agent, or particle treated with such an agent, the entrance of that agent or particle into the cell may be enhanced by the effect of the invention on the phagocytic activity of the cell, thereby increasing the efficiency of the therapeutic agent.

Although the invention has been described with regard to certain preferred embodiments, it should be understood that various changes and modifications, as would be obvious to one having the ordinary skill in this art, may be made without departing from the scope of the invention which is defined in the appended claims. For example, it may not be necessary to have the free acid at the C-terminus, as it may be amidated or substituted by some other group. Further, limited substitutions may be made to the basic tetrapeptide as illustrated by the substitution of Ser by Cys, without destroying the innerent cell attachment activity. Particular features of the invention are emphasized in the claims which follow.

Industrial Application

The invention is useful in surgery and therapeutic reconstruction and treatment of injuries.

What is claimed is:

1. A hybrid protein having cell adhesive properties, comprising a peptide of the following formula:

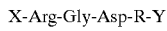

wherein X is H or one or more amino acids, Y is OH or one or more amino acids, and R is an amino acid selected from Ser, Thr, Cys, or other amino acid, and said peptide has about 31 amino acids or less, has cell attachment activity and is combined with a non-adhesive protein molecule to form a hybrid protein having cell adhesive properties.

2. A hybrid protein of claim 1, wherein the peptide has fifteen amino acids or less.

3. A hybrid protein of claim 2, wherein the peptide has ten amino acids or less.

4. A hybrid protein of claim 3, wherein the peptide has six amino acids or less.

5. A composition of matter comprising a peptide of the following formula:

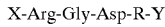

wherein X is H or one or more amino acids, Y is OH or one or more amino acids, and R is an aminc acid selected from Ser, Thr, Cys, or other amino acids, and the peptide has about 31 amino acids or less, has cell attachment activity and is coupled with a biological molecule selected from the group consisting of a collagen, glycosaminoglycan, or a proteoglycan.

6. The composition of matter of claim 5 produced by chemical means employing a cross-linker.

7. The composition of matter of claim 6, wherein the biological molecule is collagen.

8. The composition of matter of claim 7, wherein the cross-linker is 3-(2-pyridyldithio) propionic acid N-hydroxysuccinimide.

9. A composition of matter of claim 5, wherein the peptide has fifteen amino acids or less.

10. A composition of matter of claim 9, wherein the peptide has ten amino acids or less.

11. A composition of matter of claim 10, wherein the peptide has six amino acids or less.

* * * * *

UNITED STATES PATENT AND TRADEMARK OFFICE
CERTIFICATE OF CORRECTION

PATENT NO. : 5,994,501  
DATED : November 30, 1999  
INVENTOR(S) : Ruoslahti et al.

It is certified that error appears in the above-identified patent and that said Letters Patent is hereby corrected as shown below:

<u>Title page,</u>  
Item [56], References Cited, OTHER PUBLICATIONS, please delete "198-" and replace with -- 1981. --.  
Please delete "80:1224-12 1983." and replace with -- 80:1224-1227, 1983. --.

<u>Column 3,</u>  
Line 31, please delete "Lnvention" and replace with -- invention --.

<u>Column 5,</u>  
Line 8, please delete "giver," and replace with -- given, --.  
Line 40, please delete ""blockings"" and replace with -- "blocking" --.

<u>Column 7,</u>  
Line 13, please delete "innerent" and replace with -- inherent --.

Signed and Sealed this

Fifteenth Day of October, 2002

Attest:

JAMES E. ROGAN  
Attesting Officer  Director of the United States Patent and Trademark Office